United States Patent [19]

Shaver et al.

[11] Patent Number: 5,041,543

[45] Date of Patent: Aug. 20, 1991

[54] NUCLEOSIDE AND USE THEREOF

[75] Inventors: Sammy R. Shaver, Chapel Hill; George A. Freeman; Janet L. Rideout, both of Raleigh, all of N.C.

[73] Assignee: Burroughs Wellcome Co., Research Triangle Park, N.C.

[21] Appl. No.: 247,047

[22] Filed: Sep. 16, 1988

Related U.S. Application Data

[63] Continuation-in-part of Ser. No. 138,808, Dec. 28, 1987, abandoned, and a continuation-in-part of Ser. No. 168,225, Aug. 15, 1988, abandoned.

[30] Foreign Application Priority Data

Mar. 16, 1987 [GB] United Kingdom ................. 8706176

[51] Int. Cl.$^5$ ...................... C07H 17/00; A61K 31/76
[52] U.S. Cl. .................................................... 536/24
[58] Field of Search ...................... 536/23, 24; 514/49, 514/50, 51

[56] References Cited

U.S. PATENT DOCUMENTS 3,208,997 9/1965 Iwai et al. ............................. 536/23
4,395,406 7/1983 Gacek et al. .......................... 514/49

FOREIGN PATENT DOCUMENTS 0287215 10/1987 European Pat. Off. .
1958.89.1914 4/1989 Monaco .

OTHER PUBLICATIONS

Imazawa et al., J. Org Chem. 43(15): 3045–3048, 1978.
Paper–J. Med. Chem. 1983, 26, pp. 1691–1996.
Paper–Chemical Abstracts, vol. 79, 1973, p. 136.

*Primary Examiner*—John W. Rollins
*Attorney, Agent, or Firm*—Donald Brown; Lawrence A. Nielsen; Hannah O. Green

[57] ABSTRACT

A compound 1-(3-azido-2,3-dideoxy-β-D-erythro-pentofuranoxyl)-5-methyl-2(1H)-pyrimidinone and its use in a method of generating (forming, providing) 3'-azido-3'-deoxythymidine (zidovudine sometimes referred to as AZT) in the body of an animal (a mammal such as human) by systemically administering 1-(3-azido-2,3-dideoxy-β-D-erythro-pentofuranosyl)-5-methyl-2(1H)-pyriminone to said animal (mammal such as a human) is disclosed. AZT is approved and used for treating HIV infections, e.g., AIDS and ARC in humans and also has activity against gram-negative bacteria in animals.

3 Claims, No Drawings

NUCLEOSIDE AND USE THEREOF

RELATED APPLICATION

This application is a continuation-in-part of U.S. Ser. No. 07/138,808, filed Dec. 28, 1987, now abandoned and U.S. Ser. No. 07/168,225, filed Mar. 15, 1988, now abandoned.

BACKGROUND OF THE INVENTION

Zidovudine (AZT) is now a marketed product which is approved for the management of humans with symptomatic HIV infections (AIDS and advanced ARC). U.S. Pat. No. 4,724,232 issued Feb. 9, 1988 with claims to the treatment of AIDS and ARC using AZT.

The present invention is to a compound 1-(3-azido-2,3-dideoxy-β-D-erythropentofuranosyl)-5-methyl-2(1H)-pyrimidinone which when systemically administered to a mammal permits the mammal, e.g., a human, to generate (form) zidovudine in vivo to treat the HIV infection or other infection, e.g., a gram-negative bacterial infection.

BRIEF SUMMARY OF THE INVENTION

This invention is directed to a compound 1-(3-azido-2,3-dideoxy-β-D-erythropentofuranosyl)-5-methyl-2(1H)-pyrimidinone which is converted into 3'-azido-3'-deoxythymidine, also known as azidothymidine or AZT (generic name zidovudine), in the body of a mammal, e.g., human, by body enzymes. Such enzymes are believed to include xanthine oxidase/hydrogenase and/or aldehyde oxidase. AZT is a compound approved for sale to treat AIDS and ARC in humans. AZT is also active against gram-negative bacteria, e.g., *E. coli*, in animals. Thus, the compound of this invention is useful in treating HIV infections—AIDS and ARC in humans, as well as treating animals for gram-negative bacterial infections, e.g., *E. coli* infections.

The invention is also directed to the 5'-esters of 1-(3-azido-2,3-dideoxy-β-D-erythro-pentofuranosyl)-5-methyl-2(1H)-pyrimidinone and the pharmaceutically acceptable salts thereof as well as the pharmaceutically acceptable salts of 1-(3-azido-2,3-dideoxy-β-D-erythro-pentofuranosyl)-5-methyl-2(1H)-pyrimidinone.

DETAILED DESCRIPTION OF THE INVENTION

It has been found that the compound of formula (I) below is converted into 3'-azido-3'-deoxythymidine (sometimes referred to as azidothymidine or AZT), generic name zidovudine in vivo when given systemically to a mammal, e.g., a human.

It is thus possible to generate zidovudine in the body (i.e., in vivo) by systemically administering the compound of formula (I) to mammals including humans wherein the compound of formula (I) is acted upon by xanthine oxidase/dehydrogenase or aldehyde oxidase in the body and is thereby converted into zidovudine. Also, zidovudine may be synthesized, i.e., manufactured, by the ex vivo (i.e., in vitro) enzymatic oxidation of the compound of formula (I) by the action of xanthine oxidase/dehydrogenase or aldehyde oxidase on the compound of formula (I). Oxygen or other appropriate electron acceptors such as ferricyanide ion or methylene blue may serve as the oxidizing agent. Microorganisms which contain or produce xanthine oxidase/dehydrogenase may be used to effect the conversion of the compound of formula (I) into zidovudine.

Thus, in a first aspect of the present invention, there is provided the compound of formula (I):

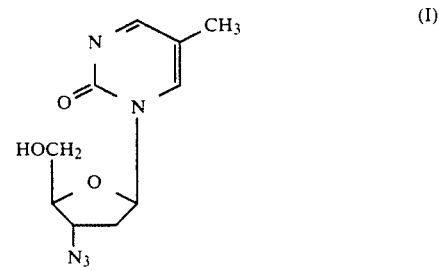

wherein the azido group is in the erythro configuration, as shown. The chemical name for the compound of formula (I) is 1-(3-azido-2,3-dideoxy-β-D-erythro-pentofuranosyl)-5-methyl-2(1H)-pyrimidinone. Also provided are the 5'-esters of the compound of formula (I) and the pharmaceutically acceptable salts thereof as well as the pharmaceutically acceptable salts of the compound of formula (I), all of which are contemplated by the terms "compound of formula (I)" and "active ingredient" as hereinafter used.

5'-Esters include the mono-, di-, and triphosphate esters as well as carboxylic acid esters. Preferred carboxylic acid esters are those wherein the non-carbonyl moiety of the ester grouping is selected from straight or branched chain $C_{1-18}$, preferably $C_{1-4}$, alkyl or alkoxyalkyl, or phenyl.

Examples of pharmaceutically acceptable salts of the compound of formula (I) as a phosphate ester include base salts, e.g, derived from an appropriate base, such as alkali metal (e.g., sodium), alkaline earth metal (e.g., magnesium), ammonium and $NX^+_4$ (wherein X is $C_{1-4}$ alkyl) salts. Examples of pharmaceutically acceptable salts of the compound of formula (I) in its unesterified form or as a carboxylic acid ester include, for example, acid addition salts of carboxylic acids such as acetic, lactic, propionic, benzoic, succinic, pivalic, acids, isethionic and methanesulfonic acids and mineral acids such as hydrochloric and sulfonic acids.

Accordingly, there is provided (a) the compound according to the invention for use in the treatment of retroviral or gram-negative bacterial infections and (b) use of the compound according to the invention in the manufacture of a medicament for the treatment or prophylaxis of a retroviral or gram-negative bacterial infection.

The compound of formula (I) also referred to herein as the active ingredient, may be administered for therapy by any suitable route including oral, rectal, nasal, topical (including transdermal buccal and sublingual), vaginal and parenteral (including subcutaneous, intramuscular, intravenous and intradermal). It will be appreciated that the preferred route will vary with the condition and age of the recipient and the nature of the infection.

In general a suitable systemic dose of the compound of formula (I) will be in the range of 4.0 to 160 mg per kilogram body weight of the recipient per day, preferably in the range of 8 to 120 mg per kilogram body weight per day and most preferably in the range 20 to 80 mg per kilogram body weight per day to generate zidovudine to treat the mammal, e.g., human, who has an HIV infection or gram negative bacterial infection. The desired dose is preferably presented as two, three, four, five, six or more sub-doses administered at appropriate intervals throughout the day. These sub-doses may be administered in unit dosage forms, for example, containing 10 to 1500 mg, preferably 20 to 1000 mg, and most preferably 50 to 700 mg of active ingredient per unit dosage form.

Suitable systemic methods of administering to a mammal, e.g., a human, the compound of formula (I) are orally or parenterally.

While it is possible for the compound of formula (I) to be administered systemically (internally) alone it is preferably to present it as a pharmaceutical formulation. The formulations of the present invention comprise the compound of formula (I) as above defined, together with one or more acceptable carriers thereof and optionally other therapeutic agents. Each carrier must be "acceptable" in the sense of being compatible with the other ingredients of the formulation and not injurious to the patient. Formulations include those suitable for oral, rectal, nasal, topical (including transdermal, buccal and sublingual), vaginal or parenteral (including subcutaneous, intramuscular, intravenous and intradermal) administration. The formulations may conveniently be presented in unit dosage form and may be prepared by any methods well known in the art of pharmacy. Such methods include the step of bringing into association of the compound of formula (I) with the carrier which constitutes one or more accessory ingredients. In general, the formulations are prepared by uniformly and intimately bringing into association the active ingredient with liquid carriers or finely divided solid carriers or both, and then if necessary shaping the product.

Formulations of the present invention suitable for oral administration may be presented as discrete units such as capsules, cachets or tablets each containing a predetermined amount of the compound of formula (I); as a powder or granules; as a solution or a suspension in an aqueous or non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the compound of formula (I) in a free-flowing form such as a powder or granules, optionally mixed with a binder (e.g., povidone, gelatin, hydroxypropylmethylcellulose) lubricant, inert diluent, preservative, disintegrant (e.g., sodium starch glycollate, cross-linked povidone, cross-linked sodium carboxymethylcellulose) surface-active or dispersing agent. Molded tablets may be made by molding in a suitable machine a mixture of the powdered compound moistened with an inert liquid diluent. The tablets may optionally be coated or scored and may be formulated so as to provide slow or controlled release of the compound of formula (I) therein.

Formulations suitable for topical administration in the mouth include lozenges comprising the active ingredient in a flavored basis, usually sucrose and acacia or tragacanth; pastilles comprising the compound of formula (I) in an inert basis such as gelatin and glycerin, or sucrose and acacia; and mouthwashes comprising the active ingredient in a suitable liquid carrier.

Formulations for rectal administration may be presented as a suppository with a suitable base comprising, for example, cocoa butter or a salicylate.

Formulations suitable for vaginal administration may be presented as pessaries, tampons, creams, gels, pastes, foams or spray formulations containing in addition to the compound of formula (I) such carriers as are known in the art to be appropriate.

Formulations suitable for parenteral administration include aqueous and non-aqueous, isotonic, sterile, injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose sealed containers, for example, ampules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit, daily sub-dose, as herein above recited, or an appropriate fraction thereof, the compound of formula (I).

The compounds according to the invention may also be presented for use in the form of veterinary formulations, which may be prepared, for example, by methods that are conventional in the art. Examples of such veterinary formulations include those adapted for:

(a) oral administration, for example drenches (e.g., aqueous or non-aqueous solutions and suspensions); tablets or boluses; powders, granules or pellets for admixture with feed stuffs; pastes for application to the tongue;

(b) parenteral administration for example by subcutaneous, intramuscular or intravenous injection, e.g., as a sterile solution or suspension; or (when appropriate) by intrammammary injection where a suspension or solution is introduced into the udder via the teat;

(c) topical application, e.g., as a transdermal patch applied to the skin; or (d) intravaginally, e.g., as a pessary, cream or foam.

It will be appreciated that such formulations as are described above will also be suitable for the presentation of combinations according to the invention, whether unitary or separate formulations, and may be prepared in a like manner.

It should be understood that in addition to the ingredients particularly mentioned above, the formulations of this invention may include other agents conventional in the art having regard to the type of formulation in question, for example, those suitable for oral administration may include such further agents as sweeteners, thickeners and flavoring agents.

The compound of formula (I), and its pharmaceutically acceptable derivatives, may be prepared in conventional manner using techniques that are well known in the art, e.g., as described in *Synthetic Procedures in Nucleic Acid Chemistry* (1, 321 (1968)), T. A. Krenitsky et al. (*J. Med. Chem.* (26, 981 (1983)); *Nucleic Acid Chemistry, Improved and New Synthetic Processes, Methods and Techniques* (Parts 1 and 2, Ed. L. D. Townsend, R. S. Tipson, (J. Wiley) 1978); J. R. Horwitz et al. (*J. Org. Chem* 29, (July 1964) 2076–78); M. Imazawa et al.

(J. Med. Chem., 45, 3274 (1980)); and R. P. Glinski et al. (J. Chem. Soc. Chem. Commun., 915 (1970)).

The present invention further includes a process for the preparation of the compound of formula (I) which comprises:

(A) reacting a compound of formula (II)

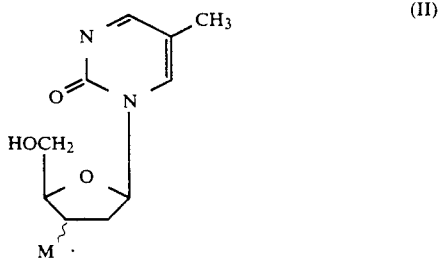

(wherein M represents a precursor group for the 3'-azido group) or a derivative (e.g., an ester) thereof, with an agent or under conditions serving to convert the said precursor group into the desired azido group;

(B) reacting a compound of formula (III)

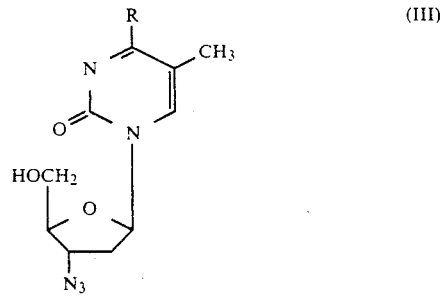

(wherein R represents a precursor group for a hydrogen atom) with an agent or under conditions serving to convert the said precursor group into the corresponding desired hydrogen atom; or (C) reacting a compound of formula (IV)

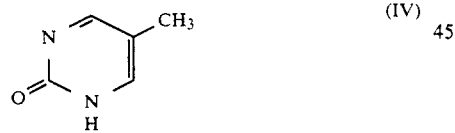

or a functional equivalent thereof, with a compound serving to introduce the desired ribofuranosyl ring at the 1-position of the compound of formula (IV);

and thereafter, or simultaneously therewith, effecting the following conversion:

when a derivative of a compound of formula (I) is formed, converting the said derivative into the parent compound of formula (I).

In the above-described process according to the invention, it will be appreciated that the choice of the precursor compounds in processes (A) to (C) will be dictated largely by the particular compound that it is desired to prepare, the above-mentioned agents and conditions being selected accordingly from those that are known in the art of nucleoside synthetic chemistry. Examples of such conversion procedures are described hereinafter for guidance and it will be understood that they can be modified in conventional manner depending on the desired compound. In particular, for example, where a conversion is described which would otherwise result in the undesired reaction of labile groups then such groups may be protected in conventional manner, with subsequent removal of the protecting groups after completion of the conversion.

Thus, for example, with regard to process (A) the group M in the compound of formula (II) may represent, for example, a halogen (e.g., chlorine), hydroxy or organosulphonyloxy (e.g., trifluoromethylsulphonyloxy, methanesulphonyloxy or p-toluenesulphonyloxy) radical.

For the preparation of the compound of formula (I), a compound of formula (II) in which the group M is a halogen (e.g., chloro) group in the threo configuration (in which the 5'-hydroxy is advantageously protected, e.g., with a trityl group) may be treated for example with lithium or sodium azide. The 3'-threo-halogen (e.g., chlorine) starting material may be obtained, for example, by reaction of the corresponding 3'-erythrohydroxy compound with, for example, triphenylphosphine and carbon tetrachloride, or alternatively by treatment with organosulphonyl halide (e.g., trifluoromethanesulphonyl chloride) to form a corresponding 3'-erythro-organosulphonyloxy compound which is then halogenated, e.g., as described above. Alternatively a 3'-threo-hydroxy compound of formula (II) may be treated, for example with triphenylphosphine, carbon tetrabromide and lithium azide to form the corresponding 3'-erythro azido compound.

With regard to process (B) the following represents an example of various procedures by which the precursor group R in formula (III) may be converted into the desired H atom:

When R represents a 1,2,4-triazol-1-yl group, such compounds may be converted to the desired compound of formula (I) by treatment with hydrazine hydrate followed by treatment with silver oxide;

With regard to process (C), this may be effected for example by treating the appropriate pyrimidine of formula (IV) or a salt or protected derivative thereof, with a compound of formula

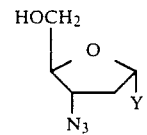

(wherein Y represents a leaving group, e.g., an acetoxy or benzoyloxy or halo (e.g., chloro) moiety, and the 5'-hydroxyl group is optionally protected, e.g., by a p-toluyl, tert-butyldimethylsilyl or tert-butyldiphenylsilyl group), and subsequently removing any protecting groups.

The following Examples are intended for illustration only and are not intended to limit the scope of the invention in any way. The term 'Active Ingredient' as used in the Examples means the compound of formula (I), i.e., 1-(3-azido-2,3-dideoxy-β-D-erythro-pentofuranosyl)-5-methyl-2(1H)-pyrimidinone.

EXAMPLE 1

Tablet Formulations

The following formulations A and B are prepared by wet granulation of the ingredients with a solution of povidone, followed by addition of magnesium stearate and compression.

|  | mg/tablet | mg/tablet |
|---|---|---|
| Formulation A | | |
| (a) Active Ingredient | 250 | 250 |
| (b) Lactose B.P. | 210 | 26 |
| (c) Povidone B.P. | 15 | 9 |
| (d) Sodium Starch Glycollate | 20 | 12 |
| (e) Magnesium Stearate | 5 | 3 |
| | 500 | 300 |
| Formulation B | | |
| (a) Active Ingredient | 250 | 250 |
| (b) Lactose | 150 | — |
| (c) Avicel pH 101 | 60 | 26 |
| (d) Povidone B.P. | 15 | 9 |
| (e) Sodium Starch Glycollate | 20 | 12 |
| (f) Magnesium Stearate | 5 | 3 |
| | 500 | 300 |
| Formulation C | | |
| Active Ingredient | 100 | |
| Lactose | 200 | |
| Starch | 50 | |
| Povidone | 5 | |
| Magnesium stearate | 4 | |
| | 359 | |

The following formulations, D and E, are prepared by direct compression of the admixed ingredients. The lactose used in formulation E is of the direct compression type (Dairy Crest- "Zeparox").

|  | mg/capsule |
|---|---|
| Formulation D | |
| Active Ingredient | 250 |
| Pregelatinized Starch NF15 | 150 |
| | 400 |
| Formulation E | |
| Active Ingredient | 250 |
| Lactose | 150 |
| Avicel | 100 |
| | 500 |

EXAMPLE 2

Capsule Formulations

Formulation A

A capsule formulation is prepared by admixing the ingredients of Formulation D in Example 1 above and filling into a two-part hard gelatin capsule. Formulation B (infra) is prepared in a similar manner.

|  | mg/capsule |
|---|---|
| Formulation B | |
| Active Ingredient | 250 |
| Lactose B.P. | 143 |
| Sodium Starch Glycollate | 25 |
| Magnesium Stearate | 2 |
| | 420 |
| Formulation C | |
| Active Ingredient | 250 |
| Macrogol 4000 B.P. | 350 |
| | 600 |

Capsules are prepared by melting the Macrogol 4000 B.P., dispersing the active ingredient in the melt and filling the melt into a two-part hard gelatin capsule.

|  | mg/capsule |
|---|---|
| Formulation D | |
| Active Ingredient | 250 |
| Lecithin | 100 |
| Arachis Oil | 100 |
| | 450 |

Capsules are prepared by dispersing the active ingredient in the lecithin and arachis oil and filling the dispersion into soft, elastic gelatin capsules.

EXAMPLE 3

Injectable Formulation

| Formulation A | | |
|---|---|---|
| Active Ingredient | | 0.200 g |
| Hydrochloric acid solution, 0.1M | q.s. to pH | 4.0 to 7.0 |
| Sodium hydroxide solution, 0.1M | q.s. to pH | 4.0 to 7.0 |
| Sterile water | q.s. to | 10 ml |

The active ingredient is dissolved in most of the water (35°-40° C.) and the pH adjusted to between 4.0 and 7.0 with the hydrochloric acid or the sodium hydroxide as appropriate. The batch was then made up to volume with the water and filtered through a sterile micropore filter into a sterile 10 ml amber glass vial (type 1) and sealed with sterile closures and overseals.

| Formulation B | |
|---|---|
| Active Ingredient | 0.125 g |
| Sterile, pyrogen-free, pH 7 phosphate buffer, q.s. to | 25 ml |

EXAMPLE 4

Intramuscular injection

|  |  | Weight (g) |
|---|---|---|
| Active Ingredient | | 0.20 |
| Benzyl alcohol | | 0.10 |
| Glycofurol 75 | | 1.45 |
| Water for injection | q.s. to | 3.00 ml |

The active ingredient is dissolved in the glycofurol. The benzyl alcohol is then added and dissolved, and water added to 3 ml. The mixture is then filtered through a sterile micropore filter and sealed in sterile 3 ml amber glass vials (type 1).

EXAMPLE 5

Syrup

| Formula A |  | Weight (g) |
|---|---|---|
| Active Ingredient | | 0.2500 |
| Sorbitol Solution | | 1.5000 |
| Glycerol | | 2.0000 |
| Sodium Benzoate | | 0.0050 |
| Flavor, Peach 17.42.3169 | | 0.0125 ml |
| Purified water | q.s. to | 5.0000 ml |

The active ingredient is dissolved in a mixture of the glycerol and most of the purified water. An aqueous solution of the sodium benzoate is then added to the solution, followed by addition of the sorbitol solution and finally the flavor. The volume is made up with purified water and mixed well.

| Formulation B | | Weight (g) |
| --- | --- | --- |
| Active Ingredient | | 0.250 |
| Sorbitol Solution | | 1.500 |
| Glycerol | | 0.005 |
| Dispersible Cellulose | | 0.005 |
| Sodium Benzoate | | 0.010 ml |
| Flavor | q.s. | |
| Purified water, q.s. to | | 5.000 ml |

Mix the sorbitol solution, glycerol and part of the purified water. Dissolve the sodium benzoate in purified water and add the solution to the bulk. Add and disperse the dispersible cellulose and flavor. Add and disperse the active ingredient. Make up to volume with purified water.

EXAMPLE 6

3'-Azido-3'-deoxythymidine (AZT)

a) 2,3'-Anhydrothymidine

Thymidine (85.4 g: 0.353 mol) was dissolved in 500 mL dry DMF and added to N-(2-chloro-1,1,2-trifluoroethyl)diethylamine (100.3 g; 0.529 mol) (prepared according to the method of D.E. Ayer, *J. Med. Chem.* 6, 608 (1963)). This solution was heated at 70° C. for 30 minutes then poured into 950 mL ethanol (EtOH) with vigorous stirring. The product precipitated from this solution and was filtered. The EtOH supernatant was refrigerated then filtered to yield the title compound. mp. =230° C.

b) 3'-Azido-3'-deoxythymidine 2,3'-O-Anhydrothymidine (25 g: 0.115 mol) and $NaN_3$ (29 g, 0.446 mol) was suspended in a mixture of 250 mL DMF and 38 mL water. The reaction mixture was refluxed for 5 hours at which time it was poured into 1 liter of water. The aqueous solution was extracted with EtOAc (3×700 mL). The EtOAc extracts were dried over $Na_2SO_4$, filtered and the EtOAc was removed in vacuo to yield a viscous oil. This oil was stirred with 200 mL water providing the title compound as a solid which was collected by filtration. mp =116°–118° C.

EXAMPLE 7

5'-O-Acetyl-3'-azido-3'-deoxythymidine

To a solution of 3'-azido-3'-deoxythymidine (AZT) 20 g) in pyridine (50 mL) at ambient temperature, acetyl chloride (2.1 equivalents) was added. The reaction was stirred for two hours and kept at 0° at 5° C. for 20 hours. It was poured onto ice water with stirring. The aqueous phase was decanted. The oily product was dissolved in ethyl acetate and extracted with water (5 times), 0.5 N hydrochloric acid, water (2x), and dried over magnesium sulphate. The solution was filtered and evaporated in vacuo. The residual oil was dissolved in chloroform, applied to a silica gel column, and flash chromatographed using 2% methanol in chloroform. Fractions with product were evaporated and the oil was chromatographed again using ethyl acetate:hexane (6:4 v/v). Fractions with product were evaporated in vacuo to give 5'-O-acetyl-3'-azido-3'-deoxythymidine as a white solid.
m.p. 96°–98° C.

Calculated: C, 46.60; H, 4.89; N, 22.65.
Found: C, 46.67; H, 4.94; N, 22.59.

EXAMPLE 8

1-(5-O-Acetyl-3-azido-2,3-dideoxy-β-D-erythro-pentofuranosyl)-5-methyl-4-(1,2,4-triazol-1-yl)-2(1H)-pyrimidinone 5'-O-Acetyl-3'-azido-3'-deoxythymidine was reacted with 5 equivalents of 1,2,4-triazole and two equivalents of 4-chlorophenyl dichlorophosphate in dry pyridine at ambient temperature for 10 days. Silica gel chromatography of the crude product using 1:1 EtOAc/hexane (v/v) followed by combination and evaporation of the appropriate fractions yielded an oil. Crystallization from EtOAc afforded the title compound as a solid 2.7 g (7.5 mMol; 60%); m.p.=143°–145° C. UV (nm): at pH 1 $\lambda_{max}$=324,245,215 ($\epsilon$=9300, 10000, 20500), $\lambda_{min}$=282,233 ($\epsilon$=2100,8200); at pH 13 $\lambda_{max}$=276 ($\epsilon$=6000), $\lambda_{min}$=242 ($\epsilon$=2000), H$^1$NMR (DMSO-d$_6$) δ9.34, 8.40(2s,2H, triazolyl), δ8.23(s,1H,H6), δ6.12(t, 1H, H1', J=6.16 Hz), β4.48–4.17(m, 4H, H3', H4', H5'), δ2.35(s, 3H, 5'-acetyl), δ2.07(s, 3H, 5CH3).

Analysis for $C_{14}H_{16}N_8O_4$.
Calculated: C, 46.67; H, 4.48; N, 31.10.
Found: C, 46.58; H, 4.51; N, 31.02.

EXAMPLE 9

1-(3-Azido-2,3-dideoxy-β-D-erythro-pentofuranosyl)-5-methyl-2-(1H)-pyrimidinone 1-(5-O-Acetyl-3-azido-2,3-dideoxy-β-D-erythro-pentofuranosyl)-5-methyl-4-(1,2,4-triazol-1-yl)-2-(1H)-pyrimidinone (0.5 g, 1.4 mMol) was dissolved in $CH_3CN$ (10 mL) and treated with 85% hydrazine hydrate (0.105 g, 2.1 mMol) for 30 minutes at ambient temperature, analogous to the procedure described in D. Cech and A. Holy, Coll. Czech. Chem. Comm. 42, 2246 (1977). The solvents were evaporated in vacuo and the residue chromatographed on silica gel with 9:1 $CHCl_3$/MeOH (v/v) as the eluting solvent. Collection and evaporation of appropriate fractions yielded a solid. The solid was dissolved in EtOH (50 mL) containing $Ag_2O$ (0.35 g, 1.5 mMol, 1.5 eq) and refluxed for 90 minutes. Filtration of the hot suspension through a bed of celite followed by removal of solvents in vacuo gave a solid. The solid was chromatographed on silica gel and eluted with 20:1 $CHCl_3$/MeOH (v/v). Combination and evaporation of appropriate fractions gave a solid which was dissolved in $NH_3$-saturated MeOH (50 mL) for 3 hours. Evaporation of the solvents in vacuo yielded an oil which was chromatographed on silica gel eluted with 20:1 $CHCl_3$/MeOH (v/v). The appropriate fractions were combined and solvents evaporated in vacuo to give an oil which slowly solidified upon standing: mp =62°–63° C.; UV (nm): at ph 1 $\lambda_{max}$=326, 212 ($\epsilon$=7700, 13000), $\lambda_{min}$=263($\epsilon$=200); at pH 13 $\lambda_{max}$322,218($\epsilon$=22700, 10800), $\lambda_{min}$=246 ($\epsilon$=400); H'NMR: (DMSO-d$_6$) δ8.46(d, 1H, H$_4$, J=3.28 Hz), 8.28(d, 1H, H$_6$, J=3.23 Hz), 6.00(t, 1H, H1', J=5.08 Hz), 5.31(t, 1H, 5'OH, J=5.12 Hz), 4.4–4.3(m, 1H, H$_3$'), 3.95–3.89(m, 1H, H$_4$'), 3.8–3.6(m, 2H, H$_5$'), 2.5–2.3(m, 2H, H$_2$'), 2.03(s, 3H, 5-CH$_3$).

Analysis calculated for $C_{10}H_{13}N_5O_3 \cdot 0.25H_2O$: C, 46.96; H, 5.32; N, 27.38.
Found: C, 47.05; H, 5.40; N, 27.14.

EXAMPLE 10

1-(5-O-Acetyl-3-azido-2,3-dideoxy-$\beta$-D-erythro-pentofuranosyl)-5-methyl-2-(1H)-pyrimidinone 1-(5-O-Acetyl-3-azido-2,3-dideoxy-$\beta$-D-pentofuranosyl)-5-methyl-4-(1,2,4-triazol-1-yl)-2-(1H)-pyrimidinone (0.5 g, 1.4 mMol) was dissolved in CH$_3$CN (10 mL) and treated with 85% hydrazine hydrate (0.105 g, 2.1 mMol) for 30 minutes at ambient temperature, analogous to the procedure described in (1). The solvents were evaporated in vacuo and the residue chromatographed on silica gel with 9:1 CHCl$_3$/MeOH (v/v) as the eluting solvent. Collection and evaporation of appropriate fractions yielded a solid. The solid was dissolved in EtOH (50 mL) containing Ag$_2$O (0.35 g, 1.5 mMol, 1.5 eq) and refluxed for 90 minutes. Filtration of the hot suspension through a bed of celite followed by removal of solvents in vacuo gave a solid. The solid was chromatographed on silica gel and eluted with 20:1 CHCl$_3$/MeOH (v/v). Combination and evaporation of appropriate fractions gave the title compound as a golden oil: UV (nm): at pH 1$\lambda_{max}$=327 ($\epsilon$=6900), $\lambda_{min}$=254 ($\epsilon$=700); at pH 13$\lambda_{max}$=322 ($\epsilon$=17200), $\lambda_{min}$=247 ($\epsilon$=600); 1H NMR: (DMSO-d$_6$) $\delta$8.46(d, J=3.13 Hz, 1H, H$_4$), 7.92(d, J=3.90 Hz, 1H, H$_6$), 6.03(dd, J=5.28 Hz, 6.64 Hz, 1H, H$_1$') 4.46-4.03(m, 4H, H$_3$', H$_4$'H$_5$'), 2.71-2.32(m, 2H, H$_2$'), 2.05, 2.04(2s, 6H, 5-CH$_3$, acetyl).

Analysis for C$_{12}$H$_{15}$N$_5$O$_4$:
Calculated: C, 49.14; H, 5.16, N, 23.88.
Found: C, 49.39; H, 5.22; N, 23.75.

(1) D. Cech and A. Holy, *Coll. Czech. Chem. Comm.* 42, 2246 (1977).

EXAMPLE 11

1-(3-Azido-2,3-dideoxy-5-O-pivaloyl-$\beta$-D-erythro-pentofuranosyl)-5-methyl-2(1H)-pyrimidinone 1-(3-Azido-2,3-dideoxy-$\beta$-D-erythro-pentofuranosyl)-5-methyl-2(1H)-pyrimidinone (0.4 g, 1.59 mMol) was dissolved in dry pyridine (10 mL) at 0° C. under a nitrogen atmosphere. Pivaloyl chloride (0.588 mL; 4.78 mMol) was added with stirring and allowed to react for 72 hours. The reaction was quenched with ice then evaporated to dryness. The residue was chromatographed on silica gel eluted with 20:1 CHCl$_3$/MeOH (v/v) and the appropriate fractions combined and evaporated to give the title compound: mp =121°-123° C.; UV (nm): at pH 1$\lambda_{max}$=327 ($\epsilon$=5900), $\lambda_{min}$=269 ($\epsilon$=820); at pH 13$\lambda_{max}$=322 ($\epsilon$=17200), $\lambda_{min}$=251 ($\epsilon$=850); 1H NMR: (DMSO-d$_6$) $\delta$8.48(d, J=3.12 Hz, 1H, H$_4$), 7.88(d, J=3.27 Hz, 1H, H$_6$), 6.02(t, J=6.25 Hz, 1H, H$_1$'), 4.48-4.39(m, 1H, H$_3$'), 4.31-4.28(m, 2H, H$_5$'), 4.20-4.14(m, 1H, H$_4$'), 2.62-2.50(m, 1H, H$_2$'), 2.41-2.27(m, 1H, H$_2$'), 2.04(s, 3H, 5-CH$_3$), 1.12(s, 9H, -C(CH$_3$)$_3$).

Analysis for C$_{15}$H$_{21}$N$_5$O$_4$.01H$_2$O.
Calculated: C, 53.43; H, 6.34, N, 20.77.
Found: C, 53.46, H, 6.36, N, 20.72.

EXAMPLE 12

1-[3-Azido-5-O-(3-chlorobenzoyl)-2,3-dideoxy-$\beta$-D-erythropentofuranosyl]-5-methyl-2(1H)-pyrimidinone The title compound was prepared from 3-chlorobenzoyl chloride in a manner analogous to the pivaloyl ester to yield a clear gum: UV (nm) pH 1$\lambda_{max}$=327 ($\epsilon$=6200), $\lambda_{min}$=264 ($\epsilon$=1700); pH 13$\lambda_{max}$=318 ($\epsilon$=8500), $\lambda_{min}$=257 ($\epsilon$=1600); 1H NMR: (DMSO-d$_6$) $\delta$8.43(d, J=1.27 Hz, 1H, H$_4$), 7.93-7.52(m, 5H, H$_6$, benzoyl), 6.06(t, J=5.28 Hz, 1H, H$_1$'), 4.67-4.51(m, 3H, H$_3$', H$_5$'), 4.30(q, J=4.25 Hz, 1H, H$_4$'), 2.59-2.39(m, 2H, H$_2$'), 1.85(s, 3H, 5-CH$_3$).

Analysis for C$_{17}$H$_{16}$N$_5$O$_4$Cl:
Calculated: C, 52.38, H, 4.14, N, 17.97.
Found: C, 52.52, H, 4.19, N, 17.82.

EXAMPLE 13

1-(3-Azido-2,3-dideoxy-5-O-hexadecanoyl-$\beta$-D-erythro-pentofuranosyl)-5-methyl-2(1H)-pyrimidinone 1-(3-Azido-2,3-dideoxy-$\beta$-D-erythro-pentofuranosyl)-5-methyl-2(1H)-pyrimidinone (0.25 g, 1 mMol) was dissolved in 11 mL anhydrous pyridine at 0° C. under a nitrogen atmosphere. Freshly distilled palmitoyl chloride (2.5 mL) was added all at once and the reaction stirred for 2 hrs. The solvents were evaporated away and the residue applied to a silica gel column eluted with 1:6 EtOAc/hexane (v/v). Appropriate fractions were combined and evaporated to give the title compound 0.14 g (0.29 mMol; 29%); mp =65°-67° C.; UV (nm) EtOH: $\lambda_{max}$=228 ($\epsilon$=13400), $\lambda_{min}$=212 ($\epsilon$=10300); 1H NMR (DMSO-d$_6$) $\delta$7.03(d, J=1.37 Hz, 1H, H$_6$), 5.90(dd, J=1.76 Hz, 6.45 Hz, 1H, H$_1$'), 5.34(s, 1H, H$_4$), 4.50(s, 1H, H$_3$'), 4.30-4.24(m, 1H, H$_4$'), 3.93-3.70(m, 2H, H$_5$'), 2.91(t, J=12.7 Hz, 2H, —C(O)CH$_2$—), 2.57-2.26(m, 2H, H$_2$'), 1.73(s, 3H, 5-CH$_3$), 1.54-0.80(m, 29 H, palmitoyl).

Analysis for C$_{26}$H$_{43}$N$_5$O$_4$.0.05C$_{16}$H$_{32}$O$_2$.
Calculated: C, 64.06, H, 8.95, N, 13.94.
Found: C, 64.28, H, 8.92, N, 13.93.

We claim:

1. 1-(3-Azido-2,3-dideoxy-$\beta$-D-erythro-pentofuranosyl)-5-methyl-2(1H)-pyrimidinone.

2. A 5'-ester of 1-(3-azido-2,3-dideoxy-$\beta$-D-erythro-pentofuranosyl)-5-methyl-2(1H)-pyrimidinone.

3. An ester according to claim 2 which is selected from the acetate, pivaloate, 3-chlorobenzoate and hexadecanoate esters.

* * * * *